United States Patent
Ducreux et al.

(10) Patent No.: US 8,393,195 B2
(45) Date of Patent: Mar. 12, 2013

(54) METHOD AND APPARATUS FOR DETECTING AND QUANTIFYING A CHEMICAL COMPOUND IN A FLUID FLOW

(75) Inventors: Olivier Ducreux, Louveciennes (FR); Fabienne Le Peltier, Rueil Malmaison (FR); Cyril Collado, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 344 days.

(21) Appl. No.: 12/669,227

(22) PCT Filed: Jun. 24, 2008

(86) PCT No.: PCT/FR2008/000893
§ 371 (c)(1),
(2), (4) Date: Sep. 27, 2010

(87) PCT Pub. No.: WO2009/016279
PCT Pub. Date: Feb. 5, 2009

(65) Prior Publication Data
US 2011/0016950 A1    Jan. 27, 2011

(30) Foreign Application Priority Data
Jul. 17, 2007  (FR) ..................... 07 05171

(51) Int. Cl.
*G01N 1/00* (2006.01)
*G01N 30/96* (2006.01)
(52) U.S. Cl. ........................ 73/28.04; 422/88
(58) Field of Classification Search ............ 73/23.2, 73/28.01, 28.04–28.06, 31.01–31.03, 31.07
See application file for complete search history.

(56) References Cited

U.S. PATENT DOCUMENTS

| | | |
|---|---|---|
| 5,301,536 A | 4/1994 | Ortega et al. |
| 5,408,868 A | 4/1995 | Ortega et al. |
| 6,455,003 B1 | 9/2002 | Anvia et al. |
| 2001/0045000 A1 | 11/2001 | Gundel et al. |
| 2004/0139785 A1* | 7/2004 | Abdul-Khalek ............. 73/28.01 |
| 2006/0243026 A1* | 11/2006 | Graze et al. ................. 73/23.31 |

FOREIGN PATENT DOCUMENTS

| | | |
|---|---|---|
| DE | 29814975 | 12/1998 |
| GB | 2 269 675 A | 2/1994 |

OTHER PUBLICATIONS

International Search Report of PCT/FR2008/000893 (Jan. 12, 2009).
English translation of pp. 6 and 7 of DE-29814975, Publication date: Dec. 24, 1998.

* cited by examiner

*Primary Examiner* — John Fitzgerald
*Assistant Examiner* — David Z Huang
(74) *Attorney, Agent, or Firm* — Millen, White, Zelano & Branican, P.C.

(57) ABSTRACT

A method and apparatus for capturing a chemical compound, typically an impurity, and for accumulating said chemical compound on a capture mass CAPT included in at least one removable adsorbent cartridge MC over a period exceeding 2 days, with a view to the external chemical analysis thereof. The apparatus ST suitable for capturing at least one chemical compound in a fluid flow for its detection and/or quantification comprise, downstream of said cartridge or cartridges, at least one device for measuring the cumulative flow which has traversed the cartridge or cartridges over a set time period. In a preferred variation of the invention, the capture mass CAPT is fragmented into a plurality of elementary masses CAPTi which allows for the spread of an irreversible adsorption front or the displacement of a chromatographic zone.

23 Claims, 3 Drawing Sheets

METHOD AND APPARATUS FOR DETECTING AND QUANTIFYING A CHEMICAL COMPOUND IN A FLUID FLOW

FIELD OF THE INVENTION

The invention relates to the field of detecting and quantifying chemical compounds, especially impurities in a fluid flow which may be a liquid or a gas.

More particularly, it relates to the detection of impurities in the form of chemical compounds the nature of which is not necessarily precisely known in advance, and/or the quantity of which is also substantially unknown, and possibly very low, for example in trace amounts.

It is not limited to particular chemical products; the only condition which is required is that these products can be captured by any physical, chemical or physico-chemical interaction.

EXAMINATION OF THE PRIOR ART

Chemical analysis is a vast field which is well known to the skilled person. A large number of chemical analysis techniques are routinely used in the industry and in laboratories; examples are gas chromatography, GC, or liquid chromatography, LC, IR (infrared) spectroscopy, MS (mass spectroscopy), NMR (nuclear magnetic resonance), X ray fluorescence, UV fluorescence, ICP (inductively coupled plasma), AA (atomic absorption), TDA-TGA (thermodifferential/thermogravimetric analysis), etc. Such techniques form part of the general field of knowledge of the skilled person.

In particular, gas or liquid phase chromatographic analysis is a widely used technique and many chemical methods use in-line chromatography which carries out spot or substantially continuous (at set time periods) analyses of one or more process streams.

However, the various analysis techniques are not suitable for all chemical compounds and all quantities of such compounds. The most reliable analyses correspond to the most favourable case in which the expected quantity of the compound under investigation, for example a known impurity, may change within a relatively narrow, known time period.

Further, impurities may occur randomly and a spot measurement may not detect an impurity which is absent at the moment of measurement but which is subsequently present.

Furthermore, systems are known which can remove a certain quantity of fluid which passes through a small cartridge or a micro-cartridge of glass containing an adsorbant which changes colour when an impurity is adsorbed and reacts with a reagent contained in the adsorbant. The micro-cartridge may include a guard mass (for prior dehydration, for example) and include a single layer of capture mass which can carry out chemisorption (reactive adsorption) with a colour change.

When this system is used in an industrial setting, for example in the oil refinery, the fluid which has traversed the micro-cartridge (effluent) is typically discharged, frequently into a waste evacuation line, for example a flare line which allows the effluent to be burned off downstream. This system is suitable for spot measurements corresponding to taking samples at a frequency which is usually every few minutes.

However, the prior art does not describe methods and apparatus which can also detect and/or quantify impurities of a nature and/or quantity which is not known in advance or which are emitted randomly in widely varying quantities over periods of several days or more. Further, there are no test methods and apparatus which can accurately quantify the distribution with time of the presence of an impurity or its interaction with a solid adsorbant or with a catalyst.

BRIEF DESCRIPTION OF THE INVENTION

In a first aspect, the present invention proposes a method which can detect the presence of and/or quantify the quantity of at least one chemical compound, for example an impurity, in a fluid flow of a nature and in a quantity which may not be known in advance, including being present in trace amounts or wherein the quantity or even the presence is variable with time or random. In accordance with a preferred variation, the method can also very accurately determine the interaction of the chemical compound with a capture mass CAPT which is typically solid, such as an adsorbant, by measuring the adsorption, capillary condensation or chemisorption of the chemical compound in several successive layers of said mass CAPT. This preferred variation of the method means that the spread, usually of a substantially irreversible adsorption front, typically a chemisorption front and/or occasionally that of a reversible adsorption front or of a capillary condensation adsorption front, generally reversible, can be measured.

In another aspect, the invention proposes a capture apparatus ST suitable for allowing the method of the invention to be carried out, allowing the detection and/or quantification of traces of such a compound.

To this end, the invention proposes a method and associated apparatus ST for capturing and concentration by long term accumulation one or more chemical compounds, for example impurity(ies), by adsorption and/or capillary condensation and/or chemisorption, ST comprising at least one removable hollow metallic adsorbant cartridge, MC, comprising a capture mass CAPT and at least one means for measuring the cumulative flow throughput or the cumulative mass throughput of fluid which has traversed the apparatus over a given time period T.

The adsorbant cartridge MC (or several cartridges MC in series) can concentrate the impurities and render them detectable after concentration and desorption or by chemical analysis, especially impurities present in trace amounts. The means for measuring the cumulative flow of fluid which has traversed the apparatus over a set time period allows the quantity of impurities measured thereby to be linked to the overall volume throughput which has traversed the apparatus, thus allowing their mean quantity in the fluid flow to be calculated.

Highly preferably, the apparatus comprises successive sections of the capture mass CAPTi which are of the same nature, allowing the spread of an adsorption or chemisorption (generally irreversible) front of a chemical compound or an impurity to be determined, or occasionally the displacement in the capture mass of an adsorption/(reversible) desorption zone (chromatographic zone) corresponding to an emission peak of an impurity.

Following analysis of the spread of the capture front in the apparatus ST, the skilled person will be able to determine the capture of the compound or impurity in the industrial reactor, the distribution of the captured compounds, determine the "breakthrough period" beyond which the compound or impurity will pass through a given zone or a guard bed, etc. It may also enable the chemical reactions in the industrial reactor to be modeled more precisely by integrating the side reactions, thermal data and/or thermodynamic and/or kinetic data into a model of the reactor.

Advantageously, not only the amount of a given chemical compound, but also the amount of one or more other chemical compounds may be quantified using successive capture masses of different natures. In a particularly advantageous variation of the invention, both the amount of a chemical compound and the moisture content are measured using a specific moisture capture mass disposed upstream of CAPT and with a reduced or zero capture capacity as regards the chemical compound.

In a variation, the invention can be used to carry out lengthy or very lengthy tests without compromising safety and without consuming excessive quantities of fluid due to sampling, by installing the ST apparatus in a bypass line. Finally, in another variation, it can quantify the amount of one or more chemical compounds at a plurality of points in a processing or chemical conversion facility using two apparatus ST and ST*.

DETAILED PRESENTATION OF THE INVENTION

More precisely, the invention provides a method for detecting the at least occasional presence of at least one chemical compound in a fluid flow of a method for the separation or chemical treatment of organic compounds, and for the quantification of at least the mean quantity of said chemical compound in the fluid flow, comprising at least the following steps:

connecting, at a point A for sampling a fluid flow, a test capture apparatus ST comprising at least one removable hollow metallic cartridge MC, preferably capable of being carried by one man, for example with a weight of less than 10 kg, comprising therein a divided capture mass CAPT which can capture said chemical compound by adsorption and/or capillary condensation and/or chemisorption, said mass being a solid or a gel and being permeable to said fluid, ST optionally comprising a plurality of said cartridges MC in series;

withdrawing and circulating a fraction of the fluid flow through the cartridge or cartridges MC for a period T of at least two days, sufficient to capture at least the major portion of the chemical compound contained in said fraction of the fluid flow, to reach at least the detection and quantification limit of said chemical compound in at least 10% of the weight of said capture mass CAPT (using the external analysis means mentioned hereinabove), and to saturate at most 95% by weight of said capture mass CAPT with said chemical compound;

measuring the cumulative flow CFL of fluid which has traversed the cartridge over the period T;

interrupting circulation of the fraction of the fluid flow in the cartridge;

removing the cartridge after depressurizing and/or flushing with a fluid which is free of said chemical compound, for example nitrogen;

opening said cartridge, optionally in an atmosphere of a fluid which is free of said chemical compound, for example nitrogen, and extracting at least a portion of said capture mass CAPT from said cartridge;

carrying out a qualitative and quantitative chemical analysis of said chemical compound in at least one fraction of CAPT and/or in the gases emitted by said fraction of CAPT after a desorption step, in analysis means which are external to the apparatus ST;

from the quantitative chemical analysis and from the value of the cumulative flow CFL of fluid which has traversed the cartridge, determining the mean quantity of the chemical compound in the fluid flow over said period T.

In accordance with the invention, the term "capture" encompasses any physical and/or chemical interaction which can retain and/or transform the chemical compound on the capture mass CAPT, especially by adsorption and/or capillary condensation and/or chemisorption. The interaction may be reversible or irreversible or partially reversible.

The method of the invention can thus capture and concentrate a chemical compound over a long period T. Subsequently, by desorbing that compound and analyzing the desorbed gases and/or by analyzing the capture mass CAPT, it enables the quantity of captured compound to be determined precisely. The measurement of the cumulative flow of fluid thus provides access to the initial concentration (or quantity) of the chemical compound in the starting fluid.

Using a plurality of specific capture masses, the method of the invention allows a plurality of chemical compounds to be captured, concentrated and quantified and possibly also allows the quantity of water present to be quantified; certain fluids which are normally dehydrated may absorb water in the storage bins and/or during their transfer.

It is also capable of allowing a determination of the amounts of chemical compound(s), for example impurity (ies), present in a random manner to be determined, for example with one or more emission peaks per day or per week, or even per month and which may be absent the rest of the time.

The method of the invention also concentrates the impurity, facilitating subsequent external chemical analysis, especially when the impurity is in trace amounts. Certain impurities are found in very low quantities, measured in ppm (parts per million, by volume or by weight), or in fractional ppms. Occasionally, they may even be present in ppb (parts per billion, by volume or by weight) or even in fractional ppbs. Concentrating the impurities on the mass CAPT allows them to be analyzed; this would in some cases be impossible from a single sample. This increased concentration is also facilitated in the case of desorption before analysis, by adjusting the pressure and the temperature of desorption.

The period T may be adapted so that at most 95%, preferably at most 60% and highly preferably at most 40% by weight of CAPT is saturated by capture of the chemical compound. The minimum quantity of saturated capture mass is considerably lower. It suffices for the compound to be detectable and quantifiable in at least 10% by weight of CAPT. This may result in a mean quantity of captured compound of more than 0.1% by weight, occasionally only more than 1 ppm (parts per million) by weight of CAPT, and even occasionally only 0.1 ppm by weight of CAPT.

The adsorbant cartridge or cartridges MC are removable, each cartridge MC typically being isolatable by upstream and downstream valves with a bypass line also provided with a valve. This means that a bypass can be used to detach the cartridge MC, the fluid continuing to circulate in another cartridge MC located upstream or downstream. It is also possible to use two cartridges MC in parallel. This allows the apparatus ST to be used on an industrial site to capture a chemical compound or compounds, and after removing the cartridge or cartridges MC, to carry out desorption or analysis of CAPT in the laboratory at a later time. Thus, the capture time, sampling time and analysis time can be decoupled.

The weight of the adsorbant cartridges (and their contents) is generally limited to 10 kg (including the capture mass CAPT), preferably limited to 6 kg, and highly preferably limited to 4 kg to facilitate their transport and to enable them to be handled easily by just one person. Thus, it is advantageous to use 2 or 3 adsorbant cartridges in series, each weighing no more than 4 or 6 kg.

The cumulative flow of fluid may typically be measured using a cumulative flow rate recorder.

The apparatus ST, however, typically also includes an instant flow rate meter which can measure and/or adjust the flow rate of the fluid traversing the apparatus.

The method is not limited to a particular adsorbant or capture mass CAPT and may use any known adsorbant/capture mass, with a physical and/or chemical interaction (chemisorption), depending on the fluid which is processed and the type of compound/impurities expected, for example activated alumina, silica gel, activated charcoal, molecular sieve (type 3A, 5A, 13X or other) or any adsorbant mass which optionally includes metals assisting in the capture of impurities, for example reduced nickel supported on alumina, zinc oxide, a mass of sulphurized copper which may or may not be supported on alumina, or other metals which are known in the prior art. Finally, it may be a catalyst, an adsorbant or a capture mass which is identical to or different from the catalyst (or adsorbant or capture mass) traversed by the fluid in the industrial unit under consideration on which the apparatus ST is installed.

In general, the period T for the capture phase is in the range from 1 week to 5 years, preferably in the range 10 days to 3 years, and may be selected as a function of the mean quantity of the compound or impurity present, in combination with the capacity of the cartridges MC. It is also possible to adapt and control the flow rate of the fluid circulating in the cartridge or cartridges MC using a metering pump or using other known flow rate control means, in order to adjust the quantity of compound or impurity traversing ST.

However, the apparatus ST of the invention can also be used to carry out short duration tests, for example of a duration in the range from one hour to 48 hours, or even of less than one hour, for example for a few minutes or fewer, if the compound or impurity is present in sufficient quantity.

In a preferred variation of the method of the invention, a fraction of the fluid flow is withdrawn and caused to circulate through the cartridge MC or, if appropriate, the set of cartridges MC in series, which in particular contain 3 to 30 (preferably 3 to 15) elementary capture masses CAPTi in series, which are physically separated and of the same nature, and a quantitative chemical analysis of the compound is carried out in at least 3 of these consecutive elementary capture masses CAPTi and/or the desorption gases from these 3 consecutive elementary capture masses CAPTi, in order to be able to measure the spread of a capture front (generally by irreversible chemisorption) of the chemical compound. This variation allows the interaction of the compound with a solid to be accurately determined, in particular with an adsorbant or a catalyst used in the industrial facility on which the method of the invention is carried out. An analysis of the capture front or a breakthrough front will enable the skilled person to determine the data and parameters of the interaction between the captured compound or impurity and the catalyst (or adsorbant or capture mass) present in the industrial unit from which the sample is taken. This means that an accurate model of what is happening in this unit (for example a catalytic reactor or an adsorption unit) can be modeled by incorporating these kinetic and/or thermodynamic data into a chemical and/or physical (adsorption) model of that unit.

ST may also comprise a plurality of elementary consecutive capture masses CAPTi of a given nature (for example n masses, with n being in the range 1 to 30, preferably in the range 3 to 15) to capture a first chemical compound, and a plurality of consecutive elementary capture masses CAPTj of another nature (for example p masses, where p is in the range 1 to 30, preferably in the range 3 to 15) to capture a second chemical compound. Three chemical compounds or more may also be captured.

The cartridge or cartridges MC may also include one or more layers of guard material, to eliminate impurities which may, for example, affect capture of the target chemical compound, or which may chemically convert certain chemical compounds into chemically transformed compounds which are easier to capture (for example organomercuric compounds transformed into metallic mercury). The apparatus ST may optionally comprise heating means to maintain the temperature or to limit the drop in temperature to a desired value in the cartridge or cartridges MC.

Compounds which are advantageously eliminated in advance include water, a highly adsorbable polar compound which can perturb or inhibit the capture of other chemical compounds. In a preferred variation of the apparatus of the invention, a fraction of the fluid flow through ST is withdrawn and circulated which includes a moisture adsorbant disposed upstream of the capture mass CAPT disposed in the cartridge MC or in at least one specific removable cartridge WR disposed upstream of MC, this moisture adsorbant generally having a capacity for capturing said chemical compound which is zero or substantially lower than that of CAPT, for example a capture capacity which is at least half, preferably at least 3 times lower and highly preferably at least 10 times lower.

Frequently, it is possible to use 3A molecular sieve which retains very few molecules. The invention can also allow the mean quantity of water contained in the fluid to be quantified, for example from a measurement of the loss on ignition of the moisture adsorbant.

Upstream of the cartridge or cartridges in series, the apparatus ST may preferably comprise two upstream adsorbant cartridges WR each comprising at least one moisture adsorbant disposed on two lines in parallel, and means for isolating and removing one of the upstream cartridges WR while the other is functioning.

In accordance with another optional feature of the method of the invention, a downstream portion of the apparatus ST downstream of the cartridge or cartridges MC is connected to a re-injection point B in a line or a volume in which the fluid flow circulates, the point B being different from point A, and a fraction of the fluid flow is circulated in ST through the cartridge or cartridges MC between said sampling point A and said re-injection point B, over the period T.

This variation is important as it allows long capture periods T to be employed without human intervention with no compromises to safety and without having to send the capture effluent into a waste evacuation line, for example an oil refinery flare line, over this long period.

Preferably, the fraction of the fluid flow in ST is circulated in a bypass between the point A located upstream and the point B located downstream, A and B each being located on a line and/or a volume in which the fluid flow circulates.

In accordance with a further characteristic feature of the method of the invention, at least two fractions of the fluid flow are withdrawn and circulated through at least two test capture apparatus: ST and ST*, ST* having the same structural characteristics mentioned above for ST, in particular those defined in claim 1, to determine the quantity of chemical compound at two different respectively upstream and downstream points. ST* is connected in a bypass between the upstream removal point A* and the downstream re-injection point B*, A* being located downstream of A. These two fractions of the fluid flow can be simultaneously and respectively circulated in a bypass in ST and ST*, then the circulations in ST and ST* are interrupted and the respective chemical analyses and determinations of the mean amounts of the chemical compound under investigation in the fractions of the fluid flow which have respectively traversed ST and ST* are analyzed. In particular, an apparatus ST or ST* may be connected to at least one withdrawal point A and/or A* located at an intermediate point of a volume, between two upstream and downstream volumes of adsorbant and/or catalyst disposed in said volume. This variation allows the presence and the mean quantity of an impurity to be determined at a plurality of points and, for example, allows the degree of saturation of a guard bed or of the degree of pollution of a catalyst or certain portions of a catalytic bed to be determined.

As an example, it is possible to use two apparatus ST and ST*, A* being located at an intermediate point and A being located upstream of the two upstream and downstream volumes of adsorbant and/or catalyst of the industrial unit to allow the presence and quantity of a chemical compound to be determined both upstream and at an intermediate point.

The method of the invention is not limited to a particular external chemical analysis means.

In a first variation, the fraction of CAPT is analyzed using a method from the group constituted by infrared spectroscopy, mass spectroscopy, nuclear magnetic resonance, X ray fluorescence, inductive coupled plasma measurement, atomic absorption, colorimetry and thermodifferential/thermogravimetric analysis.

In a second variation, an at least partial desorption step is carried out on the chemical compound of the fraction of the capture mass CAPT under reduced pressure conditions compared with the pressure during the capture step and/or at a temperature which is increased with respect to the temperature during the capture step, to obtain an effluent which comprises this chemical compound, in particular in a concentrated form, and the desorption effluents are analyzed to detect and quantify said chemical compound which has been adsorbed, using a method from the group constituted by gas chromatography or liquid chromatography, infrared spectroscopy or UV fluorescence.

It is also possible to use the two variations simultaneously, sampling and analyzing a small fraction of CAPT to initially identify the captured chemical compounds, which allows the desorption procedure and the analysis of the subsequent desorption effluents to be adjusted.

The invention also concerns a capture apparatus ST to test at least one chemical compound in a fluid flow, comprising:
  a line for supplying said fluid flow connected downstream to:
  at least one removable hollow metallic cartridge MC with a weight of less than 10 kg, or a plurality of said cartridges MC in series, each comprising at least one divided capture mass CAPT;
  at least one means for measuring the cumulative flow of fluid which has traversed said cartridge or cartridges MC over a set time period T.

Preferably, at least one cartridge MC or if appropriate the set of cartridges MC in series, contain (in particular) 3 to 30 elementary capture masses CAPTi in consecutive series, physically separated and of the same nature. As already indicated, this allows the spread of an adsorption or chemisorption front to be determined accurately, which is frequently of use in interpreting and optimizing the function of a chemical or separation facility. Further, for random impurities with emission peaks, and when these impurities are not adsorbed irreversibly, it is possible to determine the migration of an adsorption/desorption front (chromatographic zone) in the various elementary capture layers CAPTi.

Typically, 5 to 30 and preferably 6 to 20 consecutive elementary masses CAPTi are used.

In accordance with a first preferred variation of the apparatus of the invention, the elementary capture masses CAPTi in consecutive series are separated by a bed of inert beads, for example carborundum beads, or by a fibrous material, for example quartz wool.

In accordance with a second preferred variation of the apparatus of the invention, the elementary capture masses CAPTi in consecutive series are each disposed in a metallic retention structure CELL to allow them to be extracted separately from the cartridge or cartridges MC with ease. Typically, the lower portion of each of the metallic retention structures CELL includes a permeable support for the corresponding mass CAPTi, a shell section with a diameter less than the internal diameter of the corresponding cartridge MC, and a means for limiting the bypass flow around said shell section (for example a minimum functional clearance which is typically less than 1 mm, or a seal).

Usually, the cartridge MC or, if appropriate, each of said cartridges MC is cylindrical with an external diameter in the range 5 mm to 100 mm, preferably in the range 10 to 70 mm, and generally in the range 20 to 60 mm. Typically, the length to diameter ratio L/D or, if there are a plurality of cartridges, the cumulative ratio L/D, is in the range 5 to 60, preferably in the range 8 to 50 and highly preferably in the range 10 to 40.

In accordance with a preferred characteristic variation, downstream of the cartridge or cartridges MC, ST comprises a junction for connecting two downstream lines:
  the first downstream line comprising a first means for measuring the cumulative flow which is adapted to the circulation of a gaseous flow in ST; and
  the second downstream line comprising a second means for measuring said cumulative flow which is adapted to circulating a liquid flow in ST.

Thus, the apparatus ST is compatible and adapted both to capturing impurities in the gas and in the liquid phase. The flow meters and cumulative flow rate recorders used for these two phases are typically different, and so this variation of ST allows a common upstream portion comprising the adsorbant cartridge or cartridges MC to be used, which reduces the cost of the apparatus.

Each of the downstream lines advantageously comprises a means for depressurizing and/or controlling the upstream and/or downstream pressure disposed upstream of the corresponding cumulative flow measurement means.

Thus, adsorption can be carried out in the adsorbant cartridges at a high pressure encouraging adsorption (for example between 0.5 and 10 MPa, especially in the range 3 MPa to 8 MPa) and the cumulative flow of fluid can be measured after depressurization, for example between 0.1 and 0.3 MPa, especially in the range 0.1 to 0.2 MPa. The apparatus thus advantageously comprises three portions: a common upstream portion comprising one or more adsorbant cartridges MC, with a nominal pressure rating (maximum authorized pressure) which is typically at least 3 MPa, and two downstream portions (each of the downstream lines, downstream of the depressurization means), with a nominal pressure rating which is typically at most 1.2 MPa. When the apparatus ST is used in a bypass, all of the portions of ST are designed for the maximum pressure, however.

Each of the downstream lines also preferably comprises a sampling point disposed downstream of the corresponding depressurization means, for example for spot measurement of the presence of an impurity using glass tube with an internal reagent.

Upstream of the cartridge or cartridges MC in series, ST may also comprise two upstream adsorbant cartridges WR each comprising at least one solid adsorbant, disposed on two lines in parallel, and means for isolating and removing one of the upstream cartridges WR while the other is functioning.

Typically, these upstream adsorbant cartridges WR comprise a moisture adsorbant which can adsorb the water in the fluid; this water could saturate the capture mass CAPT of the cartridges MC or affect capture of the impurity being studied. The cartridges WR and/or MC may also contain one or more guard beds to eliminate one or more harmful impurities.

DESCRIPTION OF FIGURES

Referring now to FIG. 1:

Figure 1:
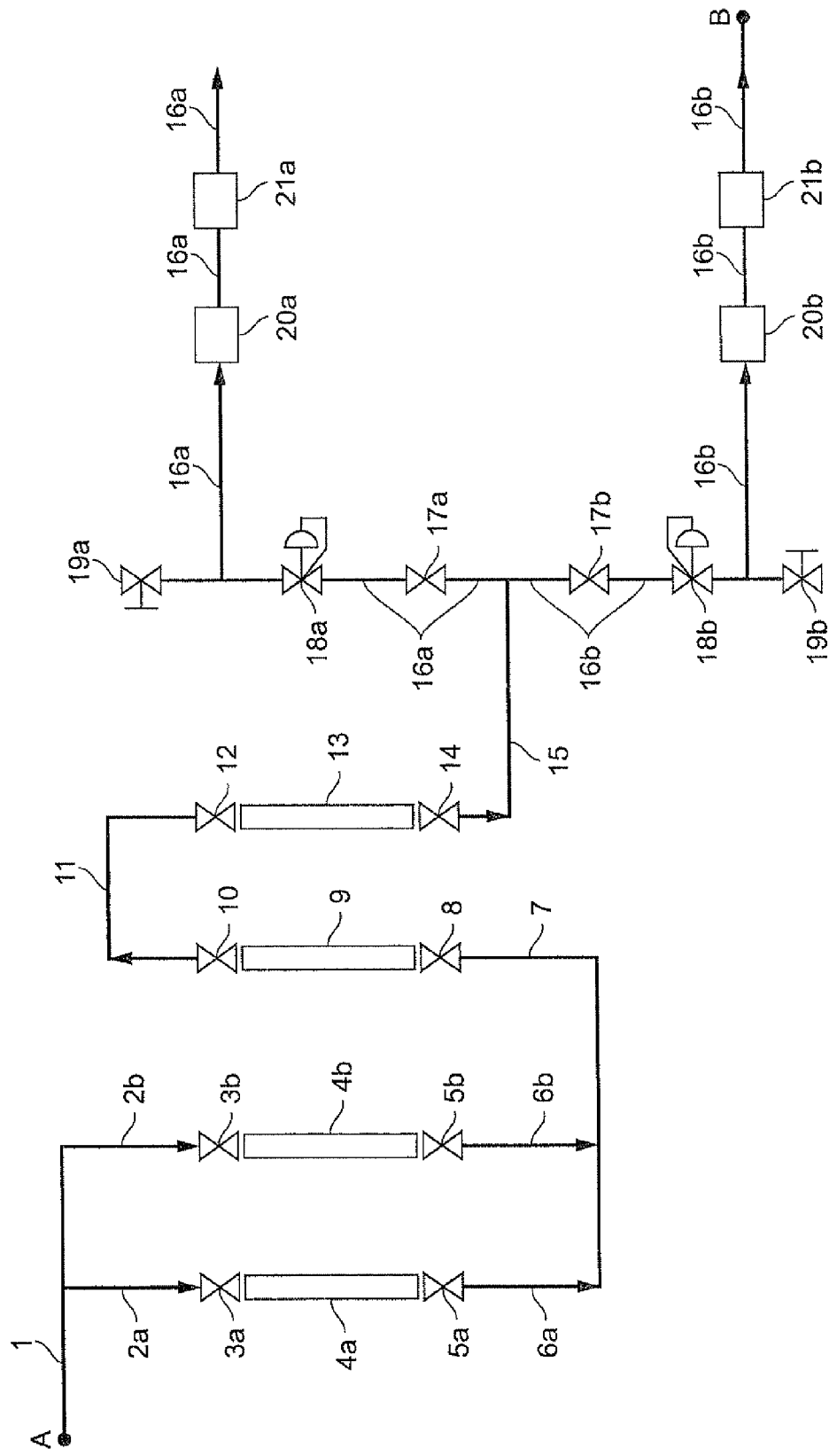
FIG. 1 is a diagrammatic representation of an apparatus ST for carrying out the method of the invention.

The apparatus comprises a line 1 for supplying a fluid flow containing impurities to be detected and to be quantified. The supply line is subdivided into two branches 2a, 6a and 2b, 6b, each comprising a removable upstream cartridge, respectively 4a and 4b, isolatable between two valves, respectively 3a, 5a and 3b, 5b. These upstream cartridges are filled with moisture adsorbant, for example 3A molecular sieve, for prior elimination of the water contained in the fluid flow, and which could affect or inhibit downstream adsorption of the chemical compounds (impurities) being investigated.

The fluid flow then rejoins the zone for capturing the chemical compounds under investigation via line 7 then 11 in two removable hollow metallic cartridges MC 9 and 13 which can be isolated between two valves, respectively 8, 10 and 12, 14. Each of the two cartridges 9 and 13 contains one or more layers which are physically separated from a suitable capture medium CAPT and may be removed without stopping the circulation in the apparatus ST and the other cartridge MC by means of a bypass line provided with a valve. The two bypass lines of cartridges 9 and 13 are not shown in the figure.

The fluid flow the impurities of which have been adsorbed then connects via line 15 to a junction to two downstream lines 16a and 16b for measuring the fluid flow and recording the total cumulative flow over a set period. Each downstream line is associated with one type of fluid, either gaseous or liquid.

As an example, line 16a, dedicated to gaseous fluids, comprises a valve 17a, a self-reducing valve 18a regulating the upstream pressure, a flow meter (instantaneous) 20a and a cumulative flow rate recorder 21a. A sampling point 19a (which may, for example, comprise a volume and a glass tube sampling point, not shown) allows a sample to be taken for spot analysis by colorimetric change.

The line 16b, dedicated to liquid fluids (the components of which are typically different from those used in a gaseous fluid) comprises the corresponding elements: 17b, 18b, 19b, 20b, and 21b.

The choice of circuit: downstream gas line 16a or downstream liquid line 16b, is made before operating the apparatus, as a function of the fluid being processed.

The apparatus may also comprise other means which are not shown, for example a valve for controlling the supply fluid flow and an instantaneous fluid flow supply meter disposed on the supply line 1. It may also comprise manometers, temperature indicators, safety valves, complementary isolation valves, temperature maintenance means, etc. . . .

The apparatus functions as follows:

After having configured the apparatus as a function of the nature of the process fluid (gas or liquid), the upstream cartridges 4a, 4b of moisture adsorbing solid are installed to initially dehydrate the process fluid in advance. Downstream, the two cartridges MC 9 and 13 containing a capture mass CAPT corresponding to the type of chemical compound or impurities which are to be detected and quantified are also installed. Preferably, the upstream cartridges will contain a moisture adsorbing solid selected to adsorb little or none of the impurities to be detected and analyzed.

The apparatus is operated for a set period T which is sufficient to capture, for example by adsorption, the chemical compound or impurity under investigation without completely saturating the adsorbant cartridges 9 and 13, for example for 15 days. The cumulative total of fluid which has traversed the apparatus ST over the adsorption period T (volume flow or mass flow) is recorded in the cumulative flow rate recorder 21a or 21b depending on the configuration used.

The adsorption period T is determined (selected) as a function of the capacity of the adsorbant cartridges and the envisaged quantity of chemical compound or impurity and may vary substantially. It is also possible to modulate the fluid flow rate traversing ST by adjusting the flow rate.

At the end of the adsorption phase T, the circulation of fluid in ST is interrupted, the apparatus is depressurized, then optionally flushed (using means which are not shown) for a short period with nitrogen. The use of a short duration is preferable so that the adsorbed impurities are not substantially desorbed. The adsorbant cartridges MC 9 and 13 are isolated and removed and the capture mass CAPT (preferably separated into 3 to 15 physically separated elementary capture masses CAPTi) is extracted for analysis in the laboratory. New adsorbant cartridges may during this time be installed to put them back into service and continue the tests on the apparatus ST.

In the laboratory, controlled desorption of the recovered adsorbant cartridges is carried out, typically at a higher temperature and in a reduced gas flow to increase the amount of compound or impurity in the desorption effluents which facilitates its detection and quantification. Thus, the compounds present are detected, along with their total quantity using conventional analysis techniques (chromatography, etc).

The fact of disposing two cartridges in series: upstream 9 and downstream 13, allows a verification that the downstream cartridge has not been saturated.

From the total flow of the compound or impurity thus measured, and from knowing the cumulative total flow of the process fluid (which would contain this compound or impurity), it is possible to deduce therefrom and quantify the mean amount of the compound or impurity initially present in the fluid flow even if this was in trace amounts or a random presence, rendering their instantaneous detection and their quantification by conventional techniques impossible.

Figure 2:
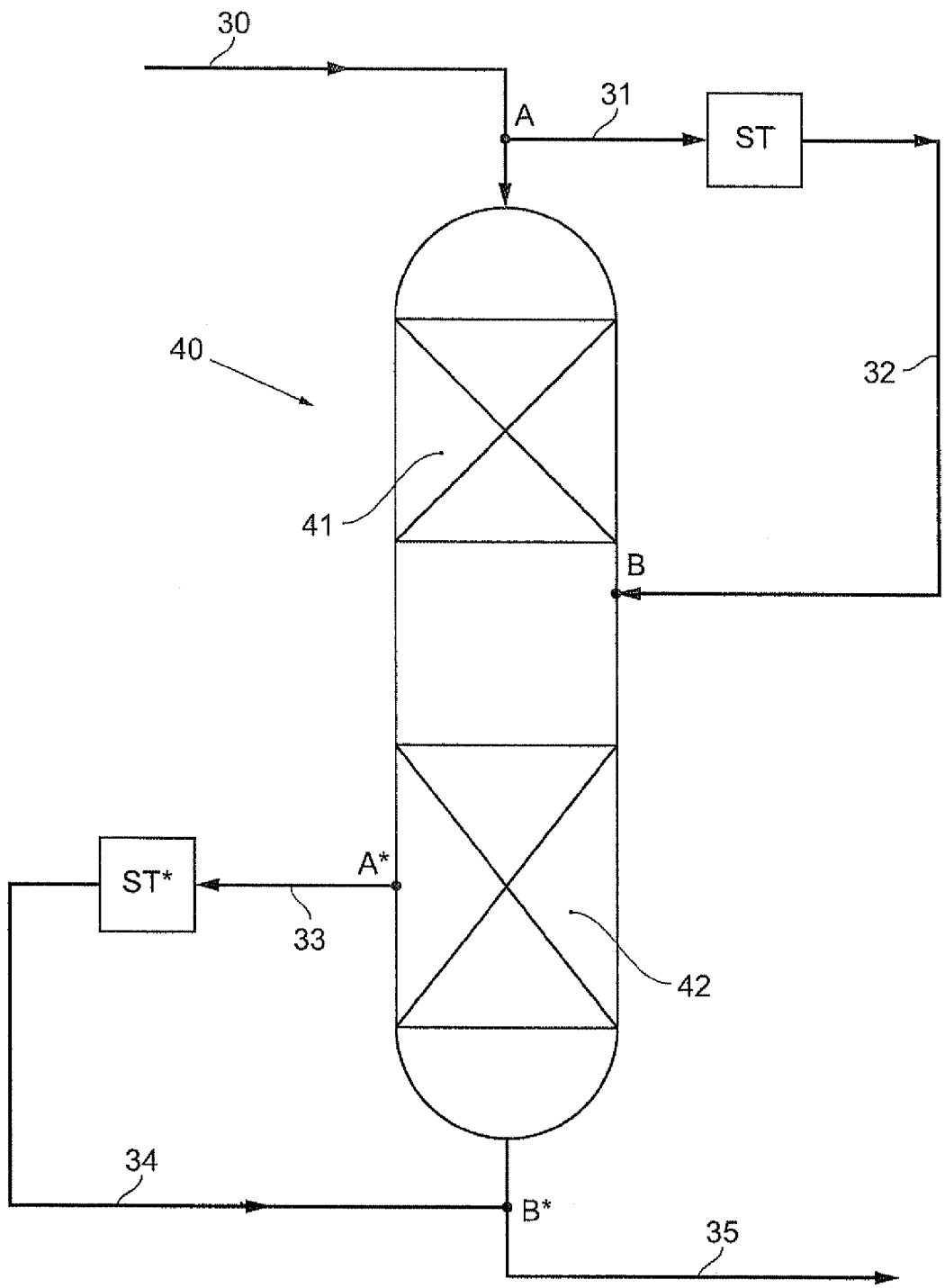
FIG. 2 is a diagrammatic representation of a reactor of a chemical facility provided with two bypass apparatus ST and ST* used to implement a variation of the method of the invention.

Referring now to FIG. 2, two apparatus ST and ST* are installed in a bypass at a plurality of points around and in a chemical reactor 40 comprising two catalytic beds 41 and 42. The reactor 40 is supplied with a fluid flow (reagents) from a line 30 and the effluent from the reactor is evacuated via a line 35.

The first capture apparatus ST, which is the furthest upstream, is connected at a point A upstream of the reactor and a very small fraction of the fluid flow (for example less than $1/1000$ or $1/10000$ of the total fluid circulating in the industrial unit) is removed, supplied to the bypass ST via the line 31, traverses ST, and the effluent from ST is re-injected into the reactor via the line 32 at a point B located between the two catalytic beds 41 and 42.

The second capture apparatus ST* which is the furthest downstream is connected at an intermediate point A* of the second catalytic bed 42 and a very small fraction of the sectional fluid flow (for example less than $1/1000$ or $1/10000$ of the total fluid) is removed, supplied as a side line ST* via the line 33, traverses ST* and the effluent from ST* is re-injected via the line 34 at a point B* located on the outlet line 35 from the reactor 40. In this configuration, it is possible both to determine the amount of impurity initially present (at point A) as well as the amount of impurity present at the intermediate point A*.

Figure 3:
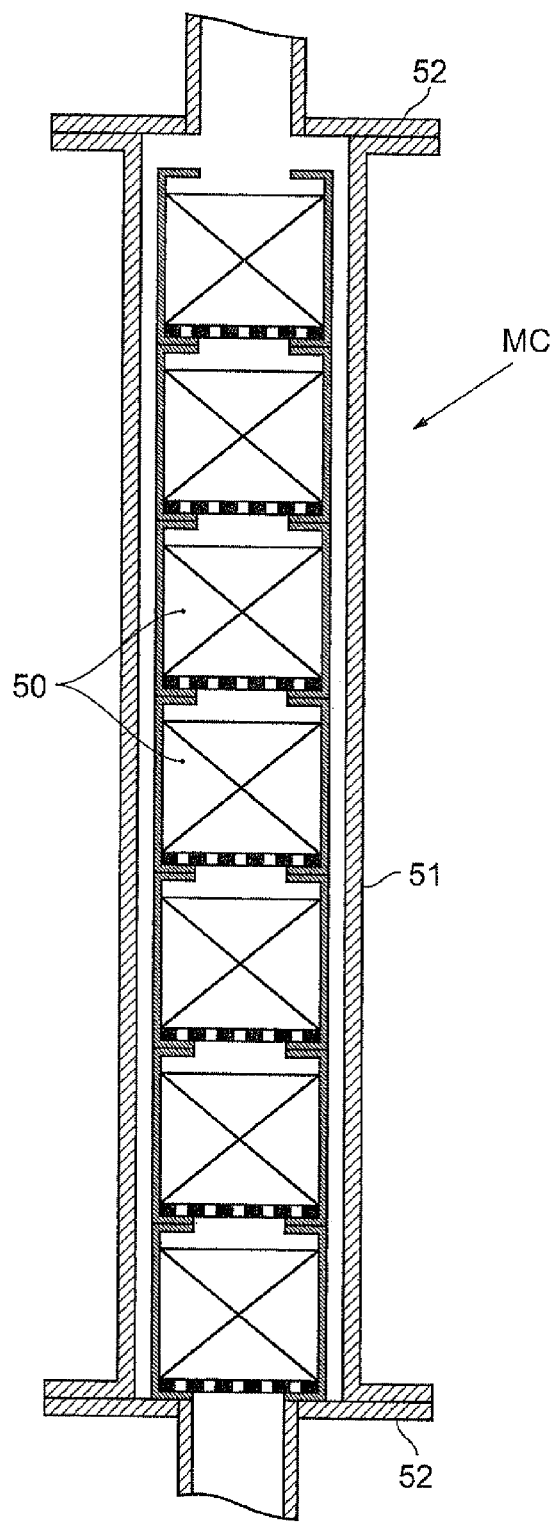
FIG. 3 is a diagrammatic representation of a preferred cartridge MC of an apparatus ST for use in carrying out the method of the invention.

Referring now to FIG. 3, this shows a capture cartridge MC of a preferred type in accordance with the invention. This cartridge comprises an elongate cylinder 51 containing 7 elementary capture masses in series 50, physically separated and which can be stacked one on top of the other to form a total capture mass. Each elementary mass is disposed in a basket comprising a screen or a perforated plate at its lower portion to retain the adsorbant mass, with opening dimensions which are sufficiently small not to allow the grains of the capture mass to pass through.

The baskets are typically self-supporting, which means that they can be stacked. The lower rim of one basket bears on the upper rim of the immediately inferior basket. The upper rim of a basket is advantageously used to grasp it and to remove it from the cartridge MC.

The baskets may be machined to leave just a minimum clearance with the metallic shell of the cartridge MC. It is also possible to provide a seal, for example a packing gasket, around each basket to prevent its capture mass from being bypassed by part of the fluid. The cartridge also comprises two removable flat bases 52 which allow the baskets to be removed. The 7 elementary capture masses in series 50 may have a number of configurations. As an example, it is possible to install one or two upstream moisture capture masses, followed by 5 or 6 elementary capture masses CAPTi or to install an upstream moisture capture mass followed by 3 elementary capture masses CAPTi then by 3 other elementary capture masses CAPTj to capture a second chemical compound, etc.

The invention is not limited to the means which have been explicitly described, and may comprise any characteristic which is already known in the fields of capture and analysis of chemical compounds.

The invention claimed is:

1. A method for detecting the at least occasional presence of at least one chemical compound in a fluid flow of a method for the separation or chemical treatment of organic compounds, and for the quantification of at least the mean quantity of said chemical compound in the fluid flow, comprising at least the following steps:

connecting, at a point A for sampling said fluid flow, a test capture apparatus (ST) comprising at least one removable hollow metallic cartridge (MC) with a weight of less than 10 kg, comprising therein a divided capture mass (CAPT) which can capture said chemical compound by adsorption and/or capillary condensation and/or chemisorption, said mass being a solid or a gel and being permeable to said fluid, said test capture apparatus (ST) optionally comprising a plurality of said cartridges (MC) in series;

withdrawing and circulating a fraction of the fluid flow through the cartridge or cartridges (MC) for a period T, sufficient to capture at least the major portion of the chemical compound contained in said fraction of the fluid flow, to reach at least the detection and quantification limit of said chemical compound in at least 10% of the weight of said capture mass (CAPT), and to saturate at most 95% by weight of said capture mass (CAPT) with said chemical compound;

measuring the cumulative flow (CFL) of fluid which has traversed the cartridge over the period T;

interrupting circulation of said fraction of the fluid flow in the cartridge;

removing said cartridge after depressurizing and/or flushing with a fluid which is free of said chemical compound;

opening said cartridge, optionally in an atmosphere of a fluid which is free of said chemical compound, and extracting at least a portion of said capture mass (CAPT) from said cartridge;

obtaining a qualitative and quantitative chemical analysis of said chemical compound in one fraction or more fractions of said capture mass (CAPT) and/or in the gases emitted by said fraction of said (CAPT) after a desorption step, from analysis means which are external to the said capture apparatus (ST);

from the quantitative chemical analysis and from the value of the cumulative flow (CFL) of fluid which has traversed the cartridge, determining the mean quantity of the chemical compound in the fluid flow over said period T.

2. A method according to claim 1, in which the period T is in the range from 1 week to 5 years.

3. A method according to claim 1, in which said fraction of the fluid flow is withdrawn and caused to circulate through the cartridge (MC) or, the set of cartridges (MC) in series, which in particular contains 3 to 30 elementary capture masses CAPTi in series, separated physically and of the same nature, and a quantitative chemical analysis of the chemical compound in at least three of said consecutive elementary capture masses CAPTi, and/or of the desorption gases from said three consecutive elementary capture masses CAPTi is then carried out, in order to be able to measure the spread of an adsorption front of said chemical compound.

4. A method according to claim 1, in which a downstream portion of the said test capture apparatus (ST) downstream of the cartridge or cartridges (MC) is connected to a point B for re-injection into a line or a volume in which said fluid flow circulates, point B being different from point A, and said fraction of the fluid flow is caused to circulate in the said test capture apparatus (ST) through the cartridge or cartridges (MC), between said removal point A and said re-injection point B during the period T.

5. A method according to claim 4, in which said fraction of the fluid flow is caused to circulate in the said test capture apparatus (ST) as a bypass between the upstream point A and the downstream point B, A and B each being located on a line and/or a volume in which said fluid flow circulates.

6. A method according to claim 5, in which at least two fractions of the fluid flow are withdrawn and caused to circulate through at least two test capture apparatuses (ST) and (ST*), to determine the amount of chemical compound at at least two different respectively upstream and downstream points, (ST*) being connected as a bypass between an upstream sampling point (A*) and a downstream re-injection point (B*), (A*) being located downstream of (A), and said two fractions of said fluid flow are caused to circulate simultaneously and respectively as a bypass in apparatuses (ST) and (ST*), then the circulations in the apparatuses (ST) and (ST*) are interrupted and respective chemical analyses and determinations of the mean quantities of the chemical compound are then obtained on the fractions of said fluid flow which have respectively traversed the apparatuses (ST) and (ST*).

7. A method according to claim 6 wherein at least two fractions of the fluid flow are withdrawn and caused to circulate simultaneously through at least the two apparatuses (ST) and (ST*), (A*) being located at said intermediate point, and A being located upstream of said two upstream and downstream volumes of adsorbent and/or catalyst.

8. A method according to claim 5 wherein an apparatus (ST) and/or (ST*) is connected to at least one sample point (A) and/or (A*) located at an intermediate point of a volume, between two upstream and downstream volumes of adsorbent and/or catalyst disposed in said volume.

9. A method according to claim 1, in which a fraction of the fluid flow is withdrawn and caused to circulate through said apparatus (ST) which comprises a moisture adsorbent disposed upstream of the capture mass CAPT, disposed in the cartridge (MC) or in at least one specific removable cartridge (WR) disposed upstream of the cartridge (MC), said moisture adsorbent having a capacity for capture of said chemical compound which is zero or substantially lower than that of said finely divided capture mass (CAPT), and both the mean moisture content and that of the chemical compound are measured in the fluid flow during said period T.

10. A method according to claim 1, in which said fraction of the capture mass (CAPT) is analyzed by a method from the group constituted by infrared spectroscopy, mass spectroscopy, nuclear magnetic resonance, X ray fluorescence, inductive coupled plasma (ICP) measurement, atomic absorption, thermodifferential/thermogravimetric analysis and colorimetry.

11. A method according to claim 1 wherein:
a) a step for at least partial desorption of the chemical compound from said fraction of the capture mass (CAPT) is carried out under pressure conditions which are reduced compared with the pressure during the capture step, and/or conditions of increased temperature compared with the temperature during the capture step, to obtain an effluent comprising said chemical compound, in particular in a concentrated form; and
b) obtaining an analysis of the desorption effluents to detect and quantify said chemical compound which has been adsorbed, using a method from the group constituted by gas chromatography GC or liquid chromatography LC, infrared spectroscopy and UV fluorescence.

12. A method according to claim 1 wherein said opening of said cartridge is conducted in an atmosphere of a fluid which is free of said chemical compound.

13. A method according to claim 1 wherein the test capture apparatus (ST) comprises a plurality of said cartridges (MC) in series.

14. A method according to claim 1 wherein said period T is at least two days.

15. A capture apparatus (ST) to test at least one chemical compound in a fluid flow, comprising:
a line for supplying said fluid flow connected downstream to:
at least one removable hollow metallic cartridge (MC) with a weight of less than 10 kg, or a plurality of said cartridges (MC) in series, each comprising at least one finely divided capture mass (CAPT); said at least one metallic cartridge (MC) or, the plurality of cartridges (MC) in series contains 3 to 30 elementary capture masses (CAPT) in consecutive series, separated physically and of the same nature;
at least one means for measuring the cumulative flow of fluid which has traversed said cartridge or cartridges (MC) over a set time period T.

16. An apparatus according to claim 15, in which said elementary capture masses (CAPTi) in consecutive series are each disposed in a metallic retention structure (CELL) allowing their separate extraction from the cartridge or cartridges (MC).

17. An apparatus according to claim 16, in which each of the metallic retention structures (CELL) comprises in its lower portion a permeable support for the corresponding capture mass (CAPTi), a shell section with a diameter which is smaller than the internal diameter of the corresponding cartridge (MC) and a means for limiting the bypass flow rate around said shell section.

18. An apparatus according to claim 15, in which said cartridge (MC) or, each of said cartridges (MC), is cylindrical with an external diameter in the range 5 mm to 100 mm, and with a length to diameter ratio L/D or, when there is a plurality of cartridges, a cumulative ratio L/D which is in the range 5 to 60.

19. An apparatus according to claim 15 further comprising, downstream of said cartridge or said cartridges (MC), a junction for connection to two downstream lines:
the first downstream line comprising a first means for measuring said cumulative flow which is adapted to the circulation of a gas flow;
and the second downstream line comprising a second means for measuring said cumulative flow which is adapted to the circulation of a liquid flow.

20. An apparatus according to claim 19, in which each of the downstream lines comprises a means for depressurizing and/or controlling the upstream and/or downstream pressure disposed upstream of the corresponding means for measuring said cumulative flow, and optionally a sampling point disposed downstream of the corresponding depressurization means.

21. An apparatus according to claim 20 further comprising said sampling point.

22. An apparatus according to claim 15 further comprising a moisture adsorbent disposed upstream of the capture mass (CAPT), disposed in the cartridge (MC) or in at least one specific removable cartridge (WR) disposed upstream of (MC), said moisture adsorbent having a capture capacity for said chemical compound which is zero or substantially lower than that of the capture mass (CAPT).

23. An apparatus according to claim 22 comprising, upstream of said cartridge or cartridges (MC), in series, two upstream adsorbent cartridges (WR) each comprising at least one moisture adsorbent disposed on two lines in parallel, and means for isolating and removing one of the upstream cartridges (WR) while the other is functioning.

* * * * *

UNITED STATES PATENT AND TRADEMARK OFFICE
CERTIFICATE OF CORRECTION

PATENT NO.       : 8,393,195 B2                                                  Page 1 of 1
APPLICATION NO.  : 12/669227
DATED            : March 12, 2013
INVENTOR(S)      : Ducreux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this

First Day of September, 2015

Michelle K. Lee
*Director of the United States Patent and Trademark Office*